United States Patent [19]

Rasmusson

[11] Patent Number: 5,380,728
[45] Date of Patent: Jan. 10, 1995

[54] ALDEHYDE METABOLITE OF 17β-N-MONOSUBSTITUTED-CARBAMOYL-4-AZA-5α-ANDROST-1-EN-3-ONES AND RELATED ANALOGUES

[75] Inventor: Gary H. Rasmusson, Watchung, N.J.

[73] Assignee: Merck & Co., Inc., Rahway, N.J.

[21] Appl. No.: 15,780

[22] Filed: Feb. 10, 1993

[51] Int. Cl.$^6$ .................................... C07D 221/02
[52] U.S. Cl. ........................................ 514/284; 546/77
[58] Field of Search ........................... 514/284; 546/77

[56] References Cited

U.S. PATENT DOCUMENTS

| | | | |
|---|---|---|---|
| 4,760,071 | 7/1988 | Rasmusson et al. | 514/284 |
| 4,845,104 | 7/1989 | Carlin et al. | 514/284 |
| 5,324,734 | 6/1994 | Gilbert | 546/77 |

OTHER PUBLICATIONS

Stinson, Chem. & Eng. News, 29 Jun. 1992 pp. 7-8.

*Primary Examiner*—Donald G. Daus
*Attorney, Agent, or Firm*—Joanne M. Giesser; Melvin Winokur; Paul D. Matukaitis

[57] ABSTRACT

17β-N-monosubstituted-carbamoyl-4-aza-5α-androst-1-en-3-ones of the formula:

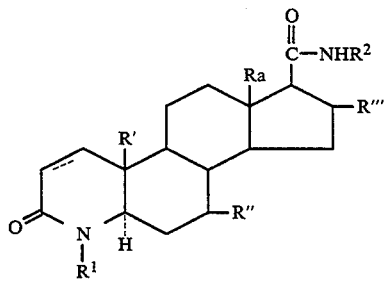

wherein
the dotted line can represent a double bond when present,
$R^1$ is selected from hydrogen, methyl and ethyl and
$R^2$ is CONHC(CH$_3$)$_2$CHO, and
Ra is methyl, are described as being useful for the treatment of benign prostatic hypertrophy.

6 Claims, No Drawings

ALDEHYDE METABOLITE OF 17β-N-MONOSUBSTITUTED-CARBAMOYL-4-AZA-5α-ANDROST-1-EN-3-ONES AND RELATED ANALOGUES

BACKGROUND OF THE INVENTION

The present invention is concerned with side chain aldehydes of 17β-N-alkyl carbamoyl-4-aza-5α-androst-1-en-3-one compounds as testosterone-5α-reductase inhibitors for the treatment of benign prostatic hypertrophy.

The art reveals that certain undesirable physiological manifestations, such as ache vulgaris, seborrhea, female hirsutism, male pattern baldness and benign prostatic hypertrophy, are the result of hyperandrogenic stimulation caused by an excessive accumulation of testosterone or similar androgenic hormones in the metabolic system.

It is now known in the art that the principal mediator of androgenic activity in some target organs is 5α-dihydrotestosterone, and that it is formed locally in the target organ by the action of testosterone-5α-reductase. It is also known that inhibitors of testosterone-5α-reductase will serve to prevent or lessen symptoms of hyperandrogenic stimulation.

For example, U.S. Pat. Nos 4,377,584, 4,220,775, 4,760,071, 4,859,681 and 5,049,562 of Rasmusson et al. describe a group of 4-aza-17β-substituted-5α-androstan-3-ones which are said to be useful in the treatment of hyperandrogenic conditions. Specifically, U.S. Pat. No. 4,760,071 describes finasteride, which is 17β-(N-tert-butylcarbamoyl)-4-aza-androst-1-ene-3-one, also known as PROSCAR ®, recently approved by the FDA for use in benign prostatic hyperplasia therapy.

U.S. Pat. No. 4,845,104 issued Jul. 4, 1989, to Merck & Co., discloses oxidized analogs of 17β-N-(monosubstituted)carbamoyl-4-aza-5α-androstan-3-ones having utility as highly potent testosterone-5α-reductase inhibitors and being metabolites resulting from in vivo administration of 7β-(N-t-butylcarbamoyl)-4-aza-5α-androst-1-en-3-one.

However, none of the cited references suggest that any of the novel- 17β-N-(monosubstituted) carbamoyl-4-aza-5α-androst-1-en-3-ones containing an aldehydes-substituted branched alkyl on the 17-position of the present invention would also be a metabolite or have utility in treating benign prostatic hypertrophy. In many cases, the metabolism of an active drug results in deactivation and/or excretion. However, in this case the compounds of the present invention maintain a high level of bioactivity in treated animals.

DESCRIPTION OF THE INVENTION

The present invention is concerned with compounds of the formula I:

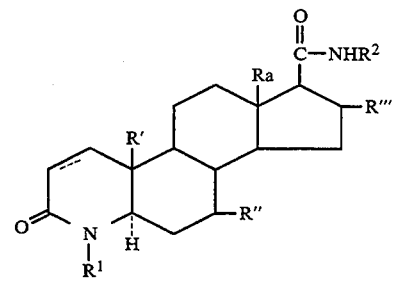

wherein
the dotted line represents a double bond which can be present;
$R^1$ is hydrogen, methyl or ethyl,
$R^2$ is $CONHC(CH_3)_2CHO$,
R' is hydrogen or methyl,
R" is hydrogen or β-methyl,
R'" is hydrogen, α-methyl or β-methyl,
Ra is methyl.

A preferred embodiment of the compounds applicable in the process of our invention is represented by the formula II:

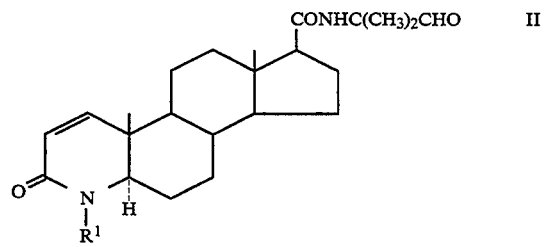

where $R^1$ is hydrogen or methyl and methyl groups of positions C-18 and C-19 are present.

The compounds of formula I of the present invention are prepared by a method starting with the known steroid of the formula 1 (See U.S. Pat. No. 4,845,104, issued Jul. 4, 1989, for its synthesis and properties):

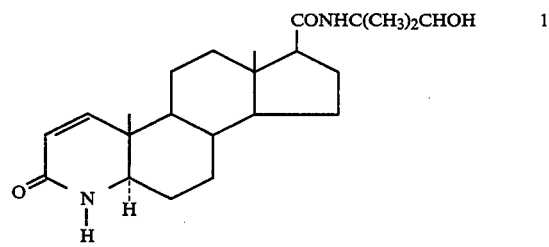

See the following Flowsheet which illustrates the stages of: (1) oxidizing said starting material 1 with e.g. pyridinium chlorochromate to produce the corresponding compound 2 and, if desired; (2) alkylating the A-ring nitrogen to introduce an N-methyl or N-ethyl substituent onto the A ring by conventional methodology, e.g. methyl iodide and sodium hydride in DMF at room temperature to produce 3; and/or (3) reducing the A-ring double bond of 2 by catalytic hydrogenation over Pd/C in EtOAc at room temperature under a hydrogen atmosphere to produce 4; and then alkylating the Ring A nitrogen by the methodology above to produce 5, or catalytically hydrogenating the double bond of 3 to produce 5. Alternatively, 2 or 4 can be alkylated with ethyl iodide.

vided in the form of scored tablets containing 0.1, 1, 5, 10, 25, 50, 100, 150, 250, and 500 milligrams of the active

FLOWSHEET

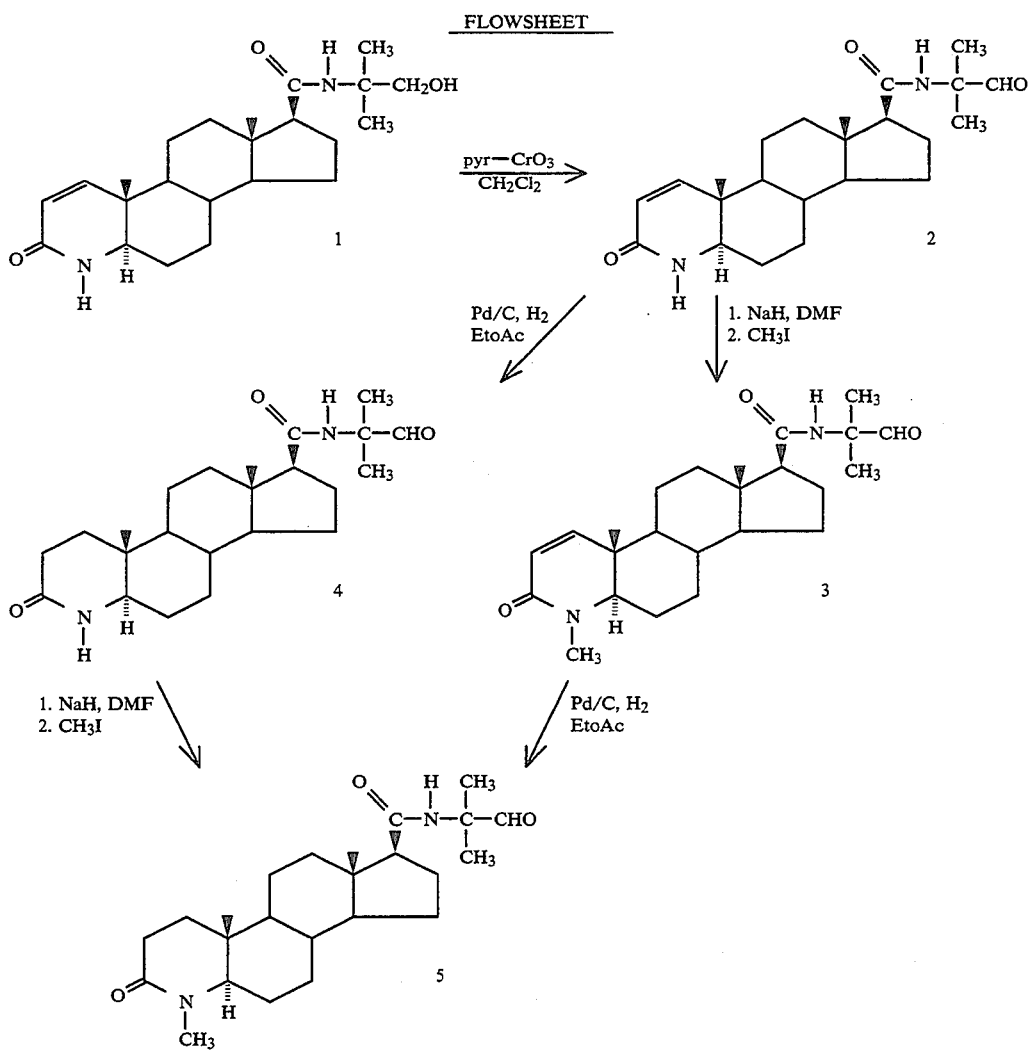

The compounds of the present invention, prepared in accordance with the method described above, are, as already described, potent and selective antiandrogens in the treatment of benign prostatic hypertrophy (BPH), by virtue of their ability to specifically inhibit testosterone-5α-reductase.

Accordingly, the present invention is particularly concerned with providing a method of treating BPH in human males by systemic or oral administration of the novel compounds of the present invention.

The present invention is thus also concerned with providing suitable topical and systemic pharmaceutical formulations for use in the novel methods of treatment of the present invention.

The compositions containing the compounds of the present invention as the active ingredient for use in the treatment of BPH can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 1 to 2,000 mg per person, preferably from 1 to 200 mg. and particularly preferred from 10 to 100 mg per person. The compositions are preferably proingredient for the symptomatic adjustment of the dosage to the patient to be treated. An effective amount of the drug is ordinarily supplied at a dosage level of from about 0.01 mg. to about 50 mg./kg. of body weight per day. Preferably the range is from about 0.1 mg. to 7 mg./kgs. of body weight per day and more preferably from about 0.5 mg to about 20 mg/kg of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methyl-cellulose and the like. Other dispersing agents which may be employed include glycerin, and the like. For parenteral administration, sterile suspensions and solutions are desired. Isotonic preparations which generally contain suitable preservative are employed when intravenous administration is desired.

The method of preparing the novel compounds of the present invention, already described above in general terms, may be further illustrated by the following examples.

EXAMPLE 1

17β-N-(2-hydroxymethyl-2-propyl) carbamoyl-4-aza-5α-androst-1-en-3-one (1)

A mixture of 100 mg of 3-oxo-4-aza-5α-androst-1-ene-17β-carboxylic acid, 69 mg of dicyclohexylcarbodiimide and 77 mg of N-hydroxybenztriazole in 5 ml of methylene chloride was stirred at 0° C. for 30 minutes and then at 24° C. for 16 hours. To the resulting solution of activated ester was added 150 μl of 2-amino-2-methylpropanol. After 5 hours the mixture was filtered and the solid was rinsed with methylene chloride. The combined tiltrates were evaporated and the residue was chromatographed on silica coated thin layer plates (4, 1000 μ×20 cm×20 cm) with 8% methanol in chloroform. The major component was extracted and isolated. Recrystallization from acetonitrile-methanol gave 41 mg of the product, m.p. 282°–287° C.

EXAMPLE 2

17β-[N-(2-oxo-1,1-dimethylethyl)]carboxamido-4-aza-5α-androst-1-en-3-one (2)

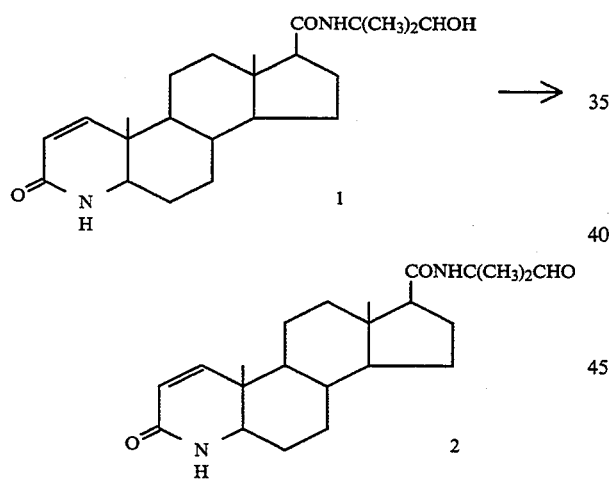

A suspension of 100 mg of the hydroxy steroid 1 in 4.0 ml of methylene chloride was treated with solid pyridinium chlorochromate (130 mg) portionwise at room temperature (RT). After stirring for 60 minutes, additional chlorochromate reagent was added (75 mg) and the mix was stirred for 2 hr more at RT. The supernatant from the reaction mixture was chromatographed by applying directly to 4×1000 μ×8"×8" silica plates and was eluted with 8% MeOH/CHCl₃. The major component was isolated (42 mg). The solid was recrystallized from EtOAc/MeOH to yield 13 mg, m.p. 277°–279° C. of product 2. Additional 2 (56 mg) could be isolated by treatment of the tarry reaction residue with 5% NaOH solution, followed by filtration, aqueous washing and drying.

What is claimed is:

1. A substantially pure compound of the formula:

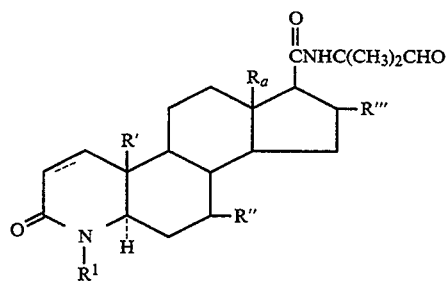

wherein:
the dotted line can represent a double bond when present;
$R^1$ is hydrogen, methyl or ethyl;
$R'$ is hydrogen or methyl;
$R''$ is hydrogen or β-methyl;
$R'''$ is hydrogen, α-methyl or β-methyl, and
$R_a$ is methyl.

2. A compound of claim 1 being:

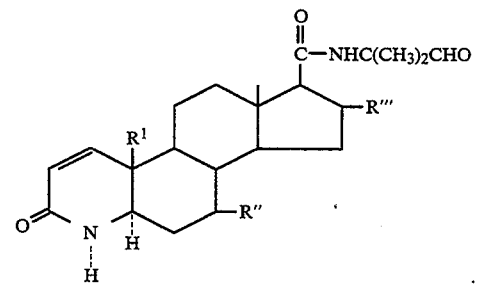

3. The compound of claim 1 being:

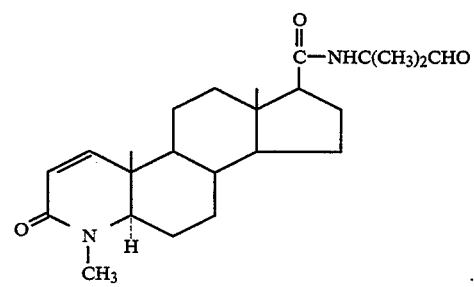

4. The compound of claim 1 being:

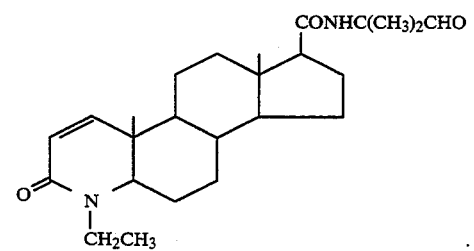

5. A method of treating the hyperandrogenic condition of acne vulgaris which comprises administering to a patient in need of such treatment a therapeutically effective amount of a compound of claim 1.

6. A pharmaceutical composition comprising a pharmaceutically acceptable carrier and an therapeutically effective amount of a compound of claim 1.

* * * * *